(12) United States Patent
Osaka et al.

(10) Patent No.: US 8,709,364 B2
(45) Date of Patent: Apr. 29, 2014

(54) HEAT RETAINING DEVICE

(75) Inventors: Akimasa Osaka, Hitachinaka (JP); Minoru Sano, Hitachinaka (JP); Hideo Kanno, Hitachinaka (JP); Akiyuki Nemoto, Mito (JP); Yoshiyuki Shoji, Mito (JP)

(73) Assignee: Hitachi-High-Technologies Corporation, Tokyo (JP)

( * ) Notice: Subject to any disclaimer, the term of this patent is extended or adjusted under 35 U.S.C. 154(b) by 0 days.

(21) Appl. No.: 13/502,271

(22) PCT Filed: Oct. 20, 2010

(86) PCT No.: PCT/JP2010/068449
§ 371 (c)(1),
(2), (4) Date: Apr. 16, 2012

(87) PCT Pub. No.: WO2011/049110
PCT Pub. Date: Apr. 28, 2011

(65) Prior Publication Data
US 2012/0207646 A1 Aug. 16, 2012

(30) Foreign Application Priority Data
Oct. 23, 2009 (JP) .................................. 2009-244768

(51) Int. Cl.
*B01L 9/06* (2006.01)
*C12M 1/02* (2006.01)
*B01L 3/00* (2006.01)
*C12M 3/00* (2006.01)

(52) U.S. Cl.
USPC ..... 422/562; 422/552; 435/286.7; 435/303.3; 435/809

(58) Field of Classification Search
USPC ................................................ 422/562, 552
See application file for complete search history.

(56) References Cited

U.S. PATENT DOCUMENTS

| | | | | |
|---|---|---|---|---|
| 4,550,841 A * | 11/1985 | Sandhaus | ........................ | 215/211 |
| 5,516,490 A * | 5/1996 | Sanadi | ............................ | 422/552 |
| 5,616,301 A * | 4/1997 | Moser et al. | ..................... | 422/64 |
| 5,675,700 A * | 10/1997 | Atwood et al. | ................ | 392/382 |
| 5,720,406 A * | 2/1998 | Fassbind et al. | ............... | 220/23.4 |
| 5,741,463 A * | 4/1998 | Sanadi | ............................ | 422/527 |
| 5,795,547 A | 8/1998 | Moser et al. | | |
| 6,555,792 B1 * | 4/2003 | Elsener et al. | ................. | 219/428 |
| 6,638,761 B2 * | 10/2003 | Shin et al. | ................... | 435/288.4 |
| 2007/0212265 A1 * | 9/2007 | Ebers et al. | ...................... | 422/99 |

FOREIGN PATENT DOCUMENTS

| JP | 60-111958 A | 6/1985 |
|---|---|---|
| JP | 02-121134 U | 10/1990 |
| JP | 06-023203 A | 2/1994 |
| JP | 06-153901 A | 6/1994 |
| JP | 7-151764 A | 6/1995 |
| JP | 2001-149801 A | 6/2001 |

* cited by examiner

*Primary Examiner* — Jill Warden
*Assistant Examiner* — Brittany Fisher
(74) *Attorney, Agent, or Firm* — Mattingly & Malur, PC (57) ABSTRACT

The present invention provides a heat retaining device for solving problematic adhesion of a container to the heat retaining device. The heat retaining device includes a supporting rod, a top plate, a bottom plate, a heat retaining body, and a supporting spring. A pressing force applied to the container contained in the hole of the heat retaining body compresses the supporting spring to move the heat retaining body downward along the supporting rod. Release of the pressing force moves the heat retaining body upward by an elastic force of the supporting spring until the heat retaining body comes into contact with the top plate.

22 Claims, 11 Drawing Sheets

Fig. 9B cross-sectional view taken along A-A

Fig. 9C

Fig. 9D cross-sectional view taken along B-B

Fig. 10A

Fig. 10B cross-sectional view taken along A-A

Fig. 10C

Fig. 10D cross-sectional view taken along B-B

HEAT RETAINING DEVICE

TECHNICAL FIELD

The present invention relates to a heat retaining device suitable for an analyzer which analyzes a biological sample.

BACKGROUND ART

Gene analyzers have been developed in recent years to automatically amplify, detect and determine genes. Such an analyzer includes a heat retaining device for retaining a biological sample at a predetermined temperature cycle. Recently, there is a demand for biological sample analyzers to have high processing speed, lower the volume of a sample and a reagent as well as shorten a temperature change time. To this end, a heat retaining device is required to improve heat transference between a container containing a biological sample and a heat retaining body.

JP 06-153901 A describes a thermostatic device enabling a container containing a reagent therein to be inserted into a hole of a heating body in a close contact state. JP 07-151764 A describes an example of fitting a hermetic-sealing closure to a container. JP 06-23203 A describes an example of a test tube evaporator including a test tube rack provided with a spring stopper. JP 02-121134 U describes an example of a closed pipet.

Patent Document 1: JP 06-153901 A
Patent Document 2: JP 07-151764 A
Patent Document 3: JP 06-23203 A
Patent Document 4: JP 02-121134 U

DISCLOSURE OF THE INVENTION

Problem to be Solved by the Invention

In order to improve heat transference between a container and a heat retaining device used for analyzer, the container is held in a close contact state with the heat retaining device. Therefore, a problem occurs that the container adheres to the heat retaining device. For instance, a hermetic-sealing closure is fitted to a container by applying a pushing force to the container. This pushing force may cause adherence of the container to the heat retaining device. The adhesion of the container to the heat retaining device makes it difficult to remove the container, thus becoming obstruction for an apparatus performing automated various steps to transfer the container to the following step. Forcibly removing the container adherent to the heat retaining device may generate a scratch on a surface of the container. Such a scratch on the container surface leads to a difficulty in optical detection of a sample contained in the container, causing a failure of precise analysis.

It is an object of the invention to cope with problematic adhesion of a container to a heat retaining device.

Means for Solving the Problem

According to the present invention, a heat retaining device includes a supporting rod, a top plate, a bottom plate, a heat retaining body, and a supporting spring. The heat retaining body is movable along the supporting rod. A pressing force applied to the container fitted in a hole of the heat retaining body compresses the supporting spring to move the heat retaining body downward along the supporting rod. Release of the pressing force moves the heat retaining body upward by an elastic force of the supporting spring until the heat retaining body comes into contact with the top plate.

Effects of the Invention

The present invention can cope with problematic adhesion of a container to a heat retaining device.

BEST MODE FOR CARRYING OUT THE INVENTION

Figure 1:
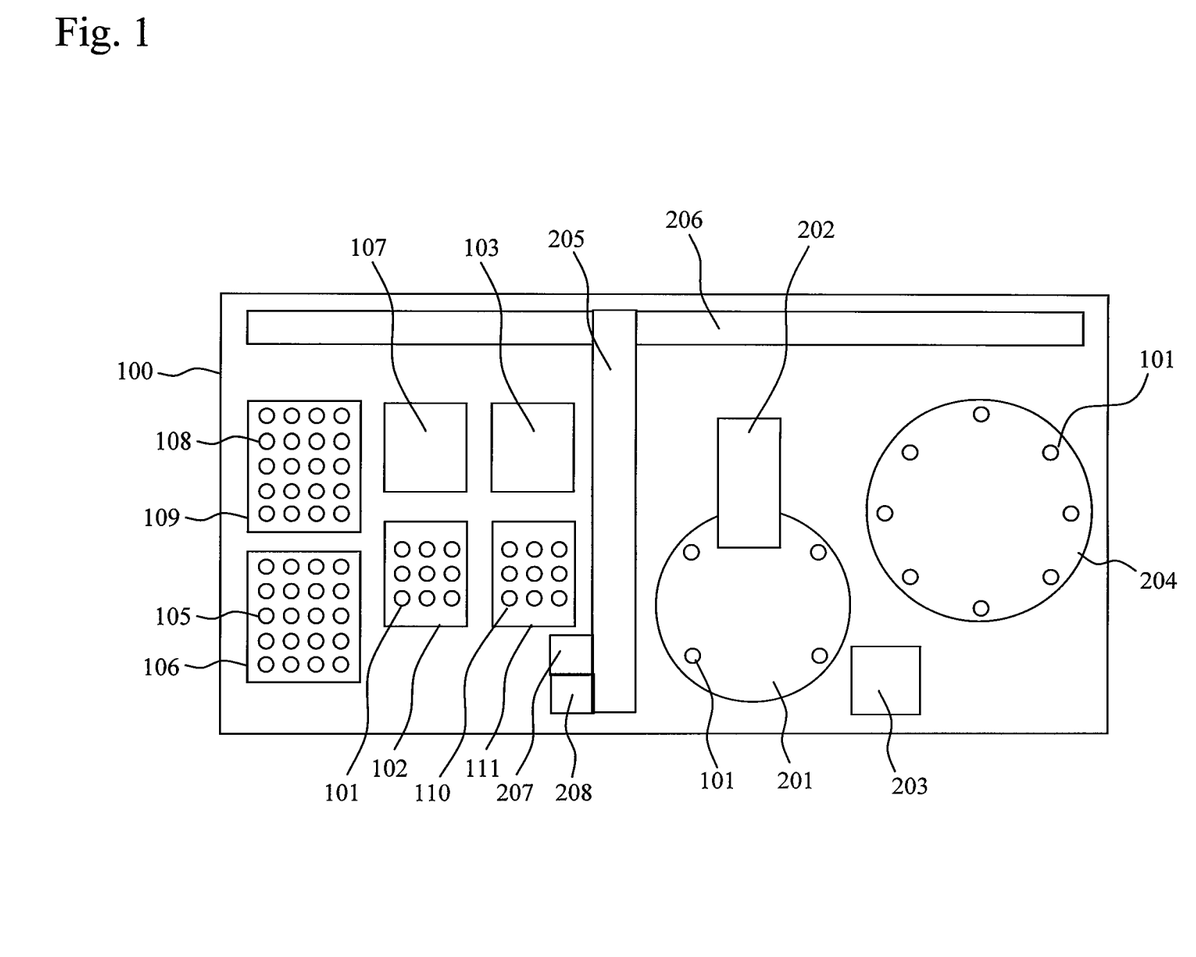
FIG. 1 schematically illustrates an analyzer according to the present invention.

Referring to FIG. 1, an exemplary analyzer according to the present invention is described below. An analyzer 100 includes a reaction container storage unit 102 for storing an unused reaction container 101, a reaction container disposal unit 103 for containing a used reaction container, a chip storage unit 106 for storing an unused chip 105, a chip disposal unit 107 for containing a used chip, a reagent container storage unit 109 for storing a reagent container 108, a specimen container storage unit 111 for storing a specimen container 110, and a robot arm 205. The robot arm 205 is provided with a dispenser 207 and a reaction container gripper 208.

The analyzer 100 further includes a heat retaining device 201 for heat retention of the reaction container 101, a hermetic-sealing closure fitting device 202 for fitting a hermetic-sealing closure to the reaction container, an agitator 203 for stirring a mixture solution including a biological sample contained in the reaction container 101, and a detector 204 for detecting a reaction product contained in the reaction container 101. In the present example, the hermetic-sealing closure fitting device 202 is provided adjacent to the heat retaining device 201, which may be provided at another position such as adjacent to the agitator 203 or at the robot arm 205. The heat retaining device 201 and the detector 204 may be a rotary type that is rotatable around a center axis. Such rotary type heat retaining device 201 and detector 204 may include a part which holds a reaction container in a cylindrical shape or a cylindrical column shape.

The robot arm 205 is provided with a driving mechanism which moves the dispenser 207 and the reaction container gripper 208 to any position in the analyzer 100. The robot arm 205 is movable along a rail 206. The dispenser 207 and the reaction container gripper 208 are movable along the robot arm 205 and further are movable vertically. Accordingly, the dispenser 207 and the reaction container gripper 208 can move freely three-dimensionally by the driving mechanism provided at the robot arm 205.

An operation of the analyzer of the present example is described below. An operation for chip replacement is described firstly. Using the robot arm 205, the dispenser 207 is transferred to above the chip disposal unit 107 to remove a used chip from the dispenser 207. The dispenser 207 is transferred to above the chip storage unit 106, and one of unused chips is fitted to the dispenser 207.

An operation for sample dispense is as follows. Using the robot arm 205, the dispenser 207 is transferred to above a specimen container 110 stored in the specimen container storage unit 111. Then, the specimen as a sample is sucked into the chip fitted to the dispenser 207. The dispenser 207 is transferred to above an unused reaction container 101 stored in the reaction container storage unit 102. Then, the specimen held by the chip is ejected to the reaction container 101. In this way, the sample is dispensed, and then using the robot arm 205, the used chip fitted to the dispenser 207 is replaced with an unused chip as stated above.

Next, an operation for reagent dispense is as follows. Using the robot arm 205, the dispenser 207 is transferred to above a reagent container 108 stored in the reagent container storage unit 109. Then, reagent is sucked into the chip fitted to the dispenser 207. The dispenser 207 is transferred to above a reaction container 101 stored in the reaction container storage unit 102. Then, the reagent held in the chip is ejected to the reaction container 101. In this way, the reaction container 101 contains mixture solution of the biological sample and the reagent.

For dispensing of a plurality of reagents, the operation for reagent dispense may be repeated. Every time a reagent is to be dispended, a chip may be replaced. Alternatively, dispense may be performed with one chip without replacing the chip. The order of sample dispense and reagent dispense may be changed as needed.

Next, using the reaction container gripper 208 provided at the robot arm 205, the reaction container 101 containing the mixture solution of the biological sample and the regent is transferred to below the hermetic-sealing closure fitting device 202. In this example, the hermetic-sealing closure fitting device 202 is provided adjacent to the heat retaining device 201. Therefore, the reaction container 101 is fitted to the heat retaining device 201. Using the hermetic-sealing closure fitting device 202, a hermetic-sealing closure is fitted to the reaction container 101. The heat retaining device 201 performs heat-retention for the mixture solution in the reaction container 101. The reaction container 101 is further conveyed to the agitator 203. The agitator 203 stirs the mixture solution in the reaction container 101. Herein, the order of heat retention by the heat retaining device 201 and stirring by the agitator 203 may be changed as needed, and both of them may be repeated as needed. Finally, using the reaction container gripper 208 provided at the robot arm 205, the reaction container 101 is transferred to the detector 204. The detector 204 detects a reaction product. The detector 204 may be configured to detect a reaction product optically, for example.

Figure 2:
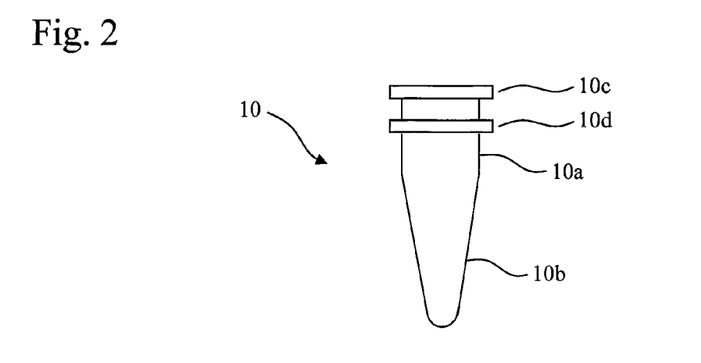
FIG. 2 illustrates an exemplary container used as a reaction container according to the present invention.

Referring now to FIG. 2, the configuration of a container 10 used as the reaction container 101 is described below. The container 10 has a cylindrical part 10a and a conical part 10b, and the cylindrical part 10a is provided with two flange parts 10c and 10d. The upper flange part 10c is provided at an upper edge of the container. The container 10 may be made of resin, preferably made of polypropylene.

Figure 3A:
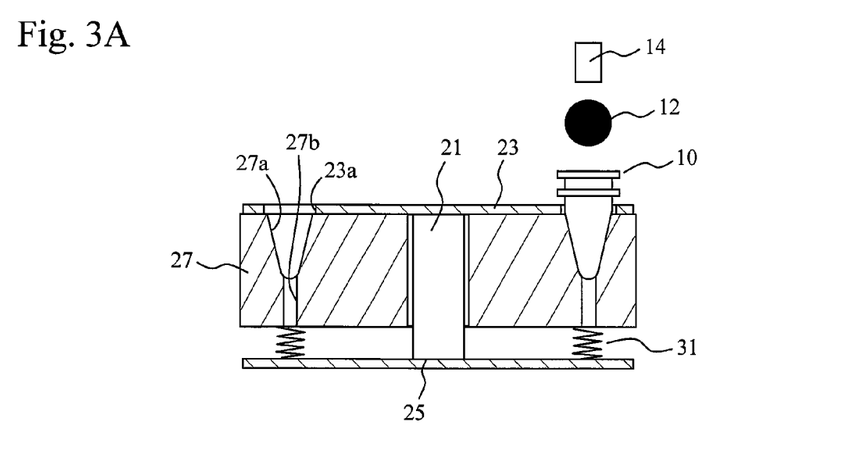
FIG. 3A illustrates a first example of a heat retaining device of an analyzer according to the present invention.
Figure 3B:
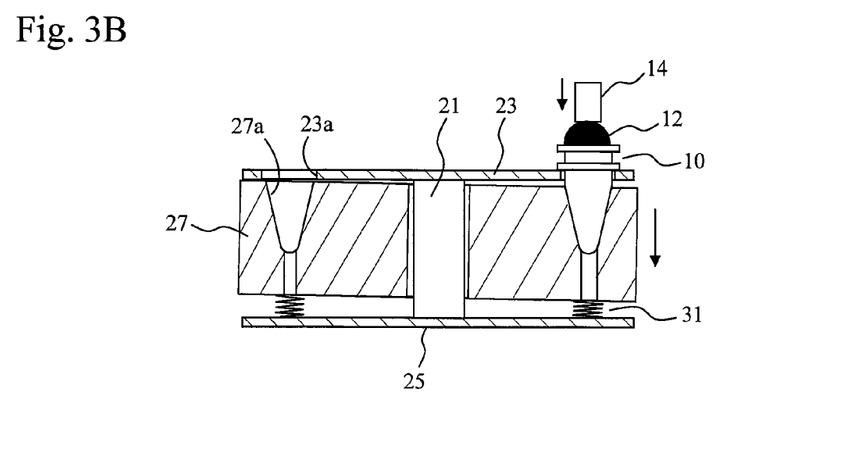
FIG. 3B illustrates a first example of a heat retaining device of an analyzer according to the present invention.

Referring to FIG. 3A and FIG. 3B, the following describes a first example of the heat retaining device of the present invention. The heat retaining device of this example includes a supporting rod 21, a top plate 23 fixed to an upper end of the supporting rod, a bottom plate 25 fixed to a lower end of the supporting rod, and a heat retaining body 27 vertically movable along the supporting rod 21. A supporting spring 31 is provided between the heat retaining body 27 and the bottom plate 25.

The top plate 23 is provided with a plurality of openings 23a. The heat retaining body 27 is provided with a plurality of holes 27a as many as the openings 23a at an upper face thereof. An opening 27b is provided at a bottom of the hole 27a. The opening 27b penetrates through the heat retaining body 27 to extend to a lower side of the heat retaining body 27.

This example describes the case in which the top plate 23 and the bottom plate 25 are circular plates and the heat retaining body 27 is in a cylindrical column shape. According to the present invention, however, the top plate 23 and the bottom plate 25 may have a form other than a circular plate, and the heat retaining body 27 may have a shape other than a cylindrical column shape. The heat retaining device of this example may be configured to rotate around a rotation axis passing through the center of the supporting rod 21.

The heat retaining body 27 is provided with a heat generating element or a heat absorbing element not illustrated, e.g., a Peltier element. Such an element is connected to a temperature controller not illustrated. The heat retaining body 27 may be made of metal with high heat conductivity such as copper or aluminum. Similarly, the top plate 23 and the bottom plate 25 also may be made of metal with high heat conductivity or may be made of the same material as that of the heat retaining body 27.

FIG. 3A illustrates the state the container 10 is disposed in the hole 27a of the heat retaining body 27. As illustrated in the drawing, the heat retaining body 27 is lifted by an elastic force of the supporting spring 31. As a result, the upper face of the heat retaining body 27 comes into contact with the top plate 23. The hole 27a of the heat retaining body 27 has an inner face of the same shape as an outer face of the conical part 10b of the container 10. Accordingly in the state in which the container 10 is contained in the hole 27a of the heat retaining body 27, the conical part 10b of the container is in face-contact with the inner face of the hole 27a of the heat retaining body. FIG. 3B illustrates the state in which a hermetic-sealing closure fitting device 14 pushes a hermetic-sealing closure 12 into the container 10. The hermetic-sealing closure 12 may be a ball made of an elastically deformable material, such as rubber or resin. The pushing force from the hermetic-sealing closure fitting device 14 to the hermetic-sealing closure 12 acts on the heat retaining body 27 via the container 10 so as to push the heat retaining body 27 down. As a result, the supporting spring 31 is compressed. When the pushing force from the hermetic-sealing closure fitting device 14 to the hermetic-sealing closure 12 is released, the heat retaining body 27 is lifted by the elastic force of the supporting spring 31 and returns to the original position. Therefore, as illustrated in FIG. 3A, the upper face of the heat retaining body 27 comes into contact with the top plate 23 again.

Figure 4A:
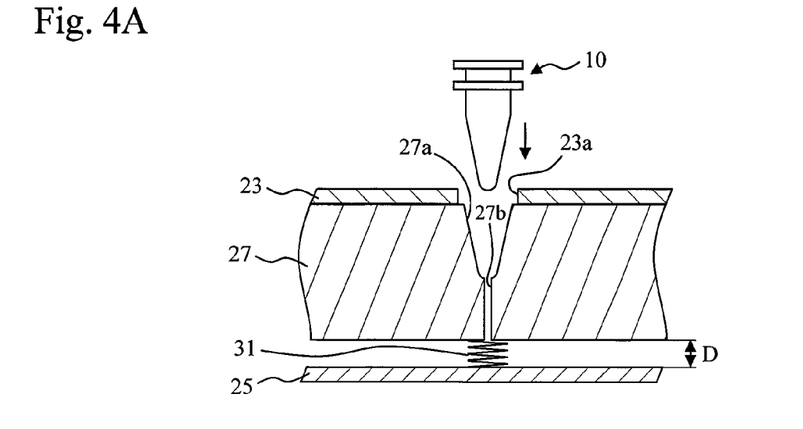
FIG. 4A explains the movement of a heat retaining body of a heat retaining device in an analyzer according to the present invention.
Figure 4B:
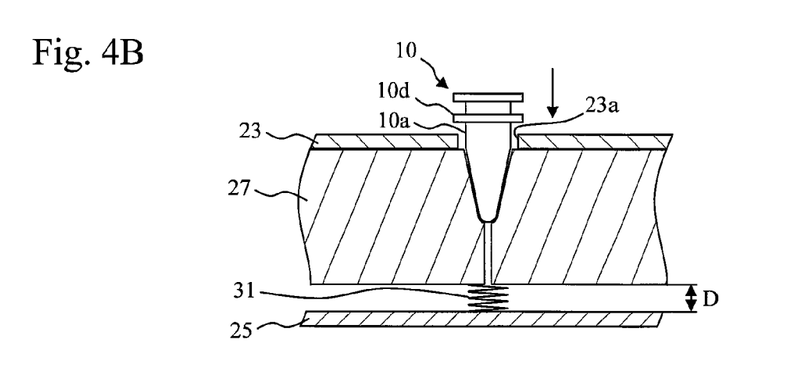
FIG. 4B explains the movement of a heat retaining body of a heat retaining device in an analyzer according to the present invention.
Figure 4C:
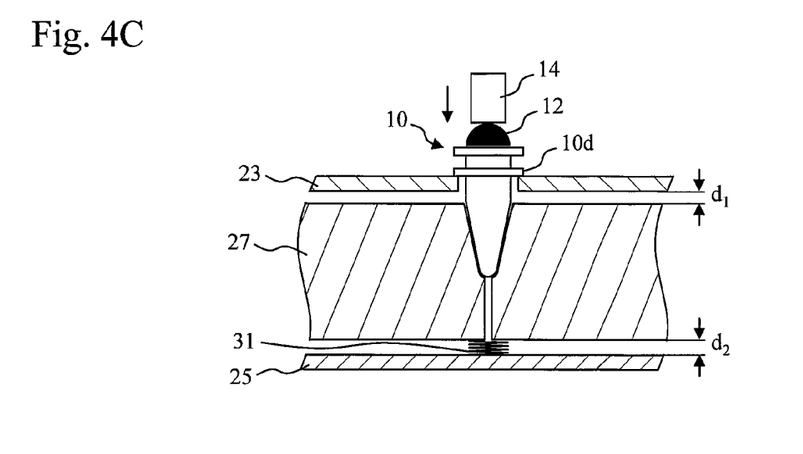
FIG. 4C explains the movement of a heat retaining body of a heat retaining device in an analyzer according to the present invention.

Referring to FIG. 4A to FIG. 4C, the force acting on the heat retaining body 27 is described below. FIG. 4A illustrates the state before the container 10 is placed in the hole 27a of the heat retaining body 27. The heat retaining body 27 is lifted by the elastic force of the supporting spring 31, so that the upper face of the heat retaining body 27 is in contact with the top plate 23. Let that a compressed amount of the supporting spring 31 in this state, i.e., an initial compressed amount is d0. Let further that the dimension between the lower face of the heat retaining body 27 and the bottom plate 25 is D. FIG. 4B illustrates the state in which the container 10 is placed in the hole 27a of the heat retaining body 27. In this state, the heat retaining body 27 does not descend yet. Therefore, the upper face of the heat retaining body 27 is in contact with the top plate 23. The dimension D of the gap between the lower face of the heat retaining body 27 and the bottom plate 25 does not change. The opening 23a of the top plate 23 has an inner diameter larger than an outer diameter of the cylindrical part 10a of the container 10 and smaller than an outer diameter of the flange part 10d.

FIG. 4C illustrates the state in which the hermetic-sealing closure fitting device 14 pushes the hermetic-sealing closure 12 into the container 10. The pushing force from the hermetic-sealing closure fitting device 14 to the hermetic-sealing closure 12 acts on the heat retaining body 27 via the container 10 so as to push the heat retaining body 27 down. When the container 10 descends until the flange part 10d of the container comes into contact with the top plate 23, the container 10 cannot move further downward. The heat retaining body 27 also cannot move further downward. In this state, let that the dimension between the upper face of the heat retaining body 27 and the top plate 23 is d1 and the dimension between the lower face of the heat retaining body 27 and the bottom plate 25 is d2. Then, d1+d2=D holds. The dimension of the gap between the lower face of the heat retaining body 27 and the bottom plate 25 is decreased by D−d2=d1. The descent of the heat retaining body 27 compresses the supporting spring 31 by d1. The compressed amount of the supporting spring 31 equals d0+d1. An elastic force Fmax corresponding to this compressed amount d0+d1 acts on the container 10 from the heat retaining body 27. As a result, the outer face (conical face) of the conical part 10b of the container 10 is brought in entire contact with the inner face (conical face) of the hole 27a. In this way, the elastic force of the supporting spring 31 pushes the heat retaining body 27 against the container 10 so that they come in close contact in this example.

When the pushing force from the hermetic-sealing closure fitting device 14 to the hermetic-sealing closure 12 is released, the heat retaining body 27 is lifted by the elastic force of the supporting spring 31 and returns to the original position. As illustrated in FIG. 4B, the upper face of the heat retaining body 27 comes into contact with the top plate 23 again. In this state, the heat retaining body 27 is pushed against the top plate 23 by the elastic force corresponding to the initial compressed amount d0 of the supporting spring 31. The force resulting from the supporting spring 31, however, does not act on the container 10.

According to this example, when the hermetic-sealing closure fitting device 14 pushes the hermetic-sealing closure 12 into the container 10 slowly, the force corresponding to the elastic force Fmax of the supporting spring 31 only acts on the container. A force larger than this elastic force Fmax does not act on the container. As stated above, the elastic force Fmax acting on the container is defined by the compressed amount d0+d1 of the supporting spring 31. That is, the elastic force Fmax acting on the container is defined by the initial compressed amount d0 and the spring constant of the supporting spring 31. By appropriately selecting the initial compressed amount d0 and the spring constant of the supporting spring 31, the force acting on the container can be set at a desired value.

Figure 5A:
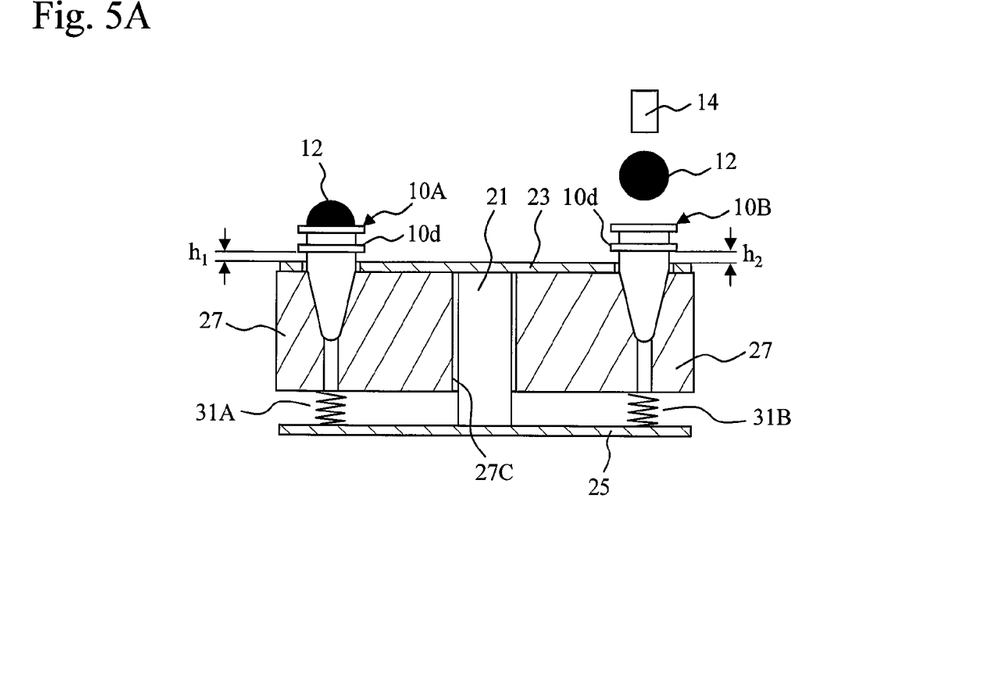
FIG. 5A explains the tilt of a heat retaining body of a heat retaining device in an analyzer according to the present invention.
Figure 5B:
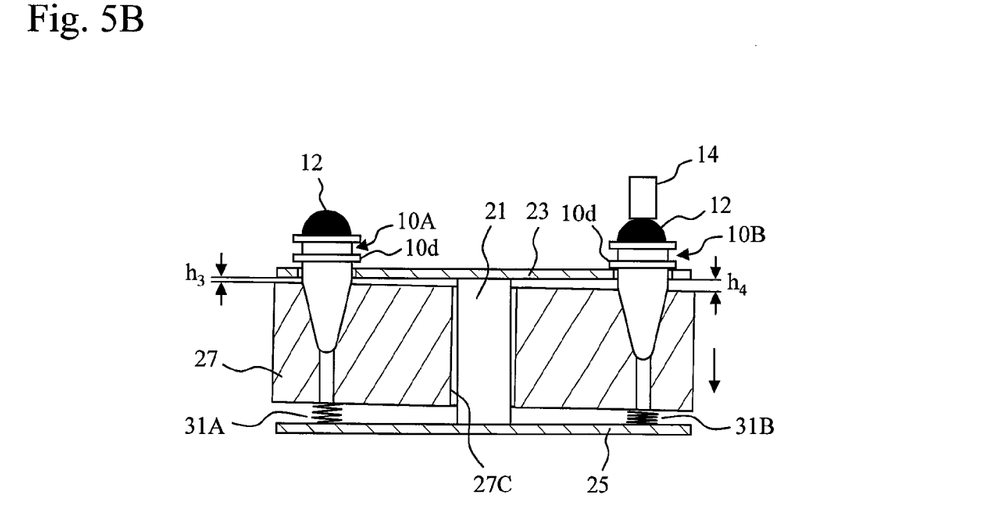
FIG. 5B explains the tilt of a heat retaining body of a heat retaining device in an analyzer according to the present invention.

Referring to FIG. 5A and FIG. 5B, the following describes tilt of the heat retaining body 27. The heat retaining body 27 of this example is capable of holding a plurality of containers. FIG. 5A illustrates the state in which two containers 10A and 10B are held at the heat retaining body 27. A hermetic-sealing closure 12 is already fitted to the first container 10A. A hermetic-sealing closure 12 is to be attached to the second container 10B from now. FIG. 5B illustrates the state in which the hermetic-sealing closure fitting device 14 pushes the hermetic-sealing closure 12 into the second container 10B. The pushing force from the hermetic-sealing closure fitting device 14 to the hermetic-sealing closure 12 acts on the heat retaining body 27 via the second container 10B so as to push the heat retaining body 27 down.

As illustrated in FIG. 5A, before the descent of the heat retaining body 27, let that the dimension of a gap between the flange part 10d of the first container 10A and the upper face of the top plate 23 is h1 and the dimension of a gap between the flange part 10d of the second container 10B and the upper face of the top plate 23 id h2. If the heat retaining device is manufactured precisely without a manufacturing error, h1=h2 holds. Therefore, when the heat retaining body 27 descends without tilting until the flange part 10d of the first container 10A comes into contact with the top plate 23, the flange part 10d of the second container 10B also comes into contact with the top plate 23 at the same time. However, the relationship may be as h1≠h2 in some cases due to a manufacturing error and the like. Herein let that h1<h2, for example. When the heat retaining body 27 descends without tilting, the flange part 10d of the first container 10A comes into contact with the top plate 23 before the flange part 10d of the second container 10B comes into contact with the top plate 23. Therefore, when the heat retaining body 27 descends until the flange part 10d of the second container 10B comes into contact with the top plate 23, the first container 10A will be detached from the hole 27a of the heat retaining body 27.

Then, in the present example, the heat retaining body 27 is configured to tilt during descending. The supporting rod 21 penetrates through the heat retaining body 27 at a center opening 27c. The supporting rod 21 has an outer diameter smaller than the inner diameter of the opening 27c of the heat retaining body 27. Therefore, there is a gap between the supporting rod 21 and the opening 27c of the heat retaining body 27. The center axis of the heat retaining body 27 can tilt by the dimension of this gap with respect to the center axis of the supporting rod 21. Let that the dimension between the upper face of the heat retaining body 27 and the top plate 23 on the periphery of the first container 10A is d3 and the dimension between the upper face of the heat retaining body 27 and the top plate 23 on the periphery of the second container 10B is d4. When the hermetic-sealing closure 12 is fitted to the second container 10B, the heat retaining body 27 tilts and the relationship d3<d4 holds. Since the heat retaining body 27 descends while tilting, when the flange part 10d of the second container 10B comes into contact with the top plate 23, the flange part 10d of the first container 10A does not come into contact with the top plate 23. That is, even when the heat retaining body 27 descends until the flange part 10d of the second container 10B comes into contact with the top plate 23, the first container 10A is not detached from the hole 27a of the heat retaining body 27.

Figure 6A:
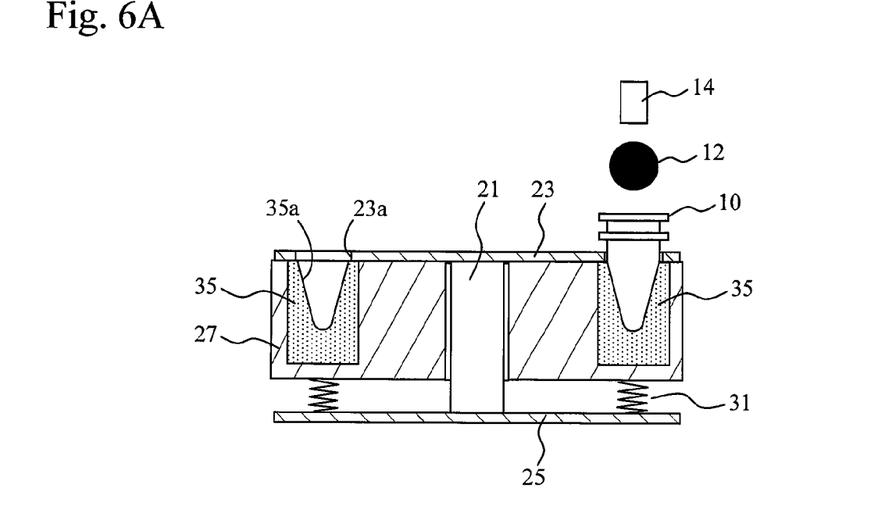
FIG. 6A illustrates a second example of a heat retaining device of an analyzer according to the present invention.
Figure 6B:
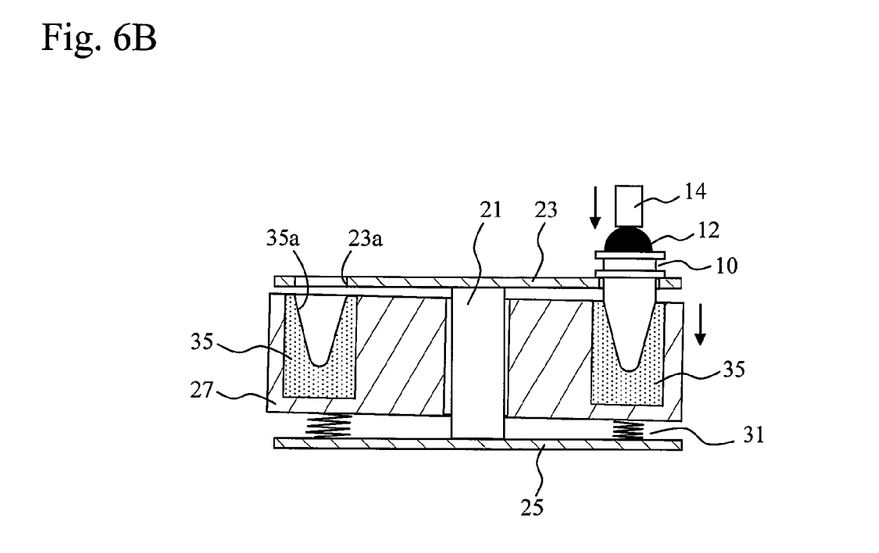
FIG. 6B illustrates a second example of a heat retaining device of an analyzer according to the present invention.

Referring to FIG. 6A and FIG. 6B, the following describes a second example of the heat retaining device of the present invention. The heat retaining device of this example includes a supporting rod 21, a top plate 23 fixed to an upper end of the supporting rod, a bottom plate 25 fixed to a lower end of the supporting rod and a heat retaining body 27 vertically movable along the supporting rod 21. A supporting spring 31 is provided between the heat retaining body 27 and the bottom plate 25.

The top plate 23 is provided with a plurality of openings 23a. The heat retaining body 27 is provided with an elastic body 35. The elastic body 35 is provided so that the heat retaining body 27 and the elastic body 35 are coplanar at their upper faces. The elastic body 35 is provided with a plurality of holes 35a as many as the openings 23a at an upper face thereof. The elastic bodies 35 may be provided as many as the openings 23a of the top plate 23 corresponding thereto, or may be formed with one ring-shaped elastic member. Although not illustrated, an opening may be formed extending from the bottom of the hole 35a to the lower side of the heat retaining body 27. The elastic body 35 may be made of an elastic material with high heat conductivity.

FIG. 6A illustrates the state in which the container 10 is disposed in a hole 35a of the elastic body 35. As illustrated in the drawing, the heat retaining body 27 is lifted by an elastic force of the supporting spring 31, so that the upper faces of the heat retaining body 27 and the elastic body 35 come into contact with the top plate 23. The hole 35a of the elastic body 35 has the inner face of the same shape as the outer face of the conical part 10b of the container 10. Accordingly, in the state in which the container 10 is contained in the hole 35a of the elastic body 35, the conical part 10b of the container is in face-contact with the inner face of the hole 35a of the elastic body. FIG. 6B illustrates the state in which a hermetic-sealing closure fitting device 14 pushes a hermetic-sealing closure 12 into the container 10. The pushing force from the hermetic-sealing closure fitting device 14 to the hermetic-sealing closure 12 acts on the elastic body 35 via the container 10 so as to push the heat retaining body 27 down. As a result, at least one of the elastic body 35 and the supporting spring 31 is compressed. When the flange part 10d of the container comes into contact with the top plate 23, the container cannot move further downward. In this example, the elastic force from the elastic body 35 and the supporting spring 31 pushes the elastic body 35 against the container 10, so that they come into close contact.

When the pushing force from the hermetic-sealing closure fitting device 14 to the hermetic-sealing closure 12 is released, the heat retaining body 27 is lifted by the elastic force of the supporting spring 31 and returns to the original position. Therefore, the upper face of the elastic body 35 comes into contact with the top plate 23 again.

Figure 7A:
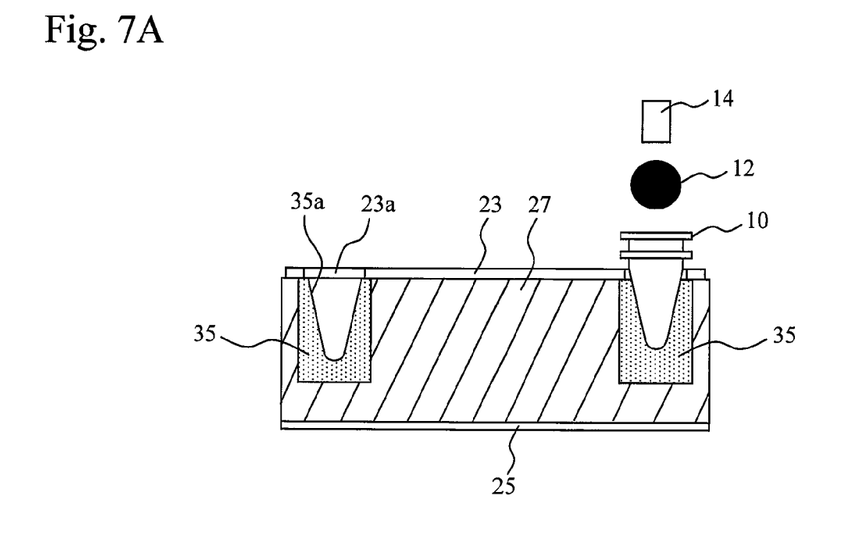
FIG. 7A illustrates a third example of a heat retaining device of an analyzer according to the present invention.
Figure 7B:
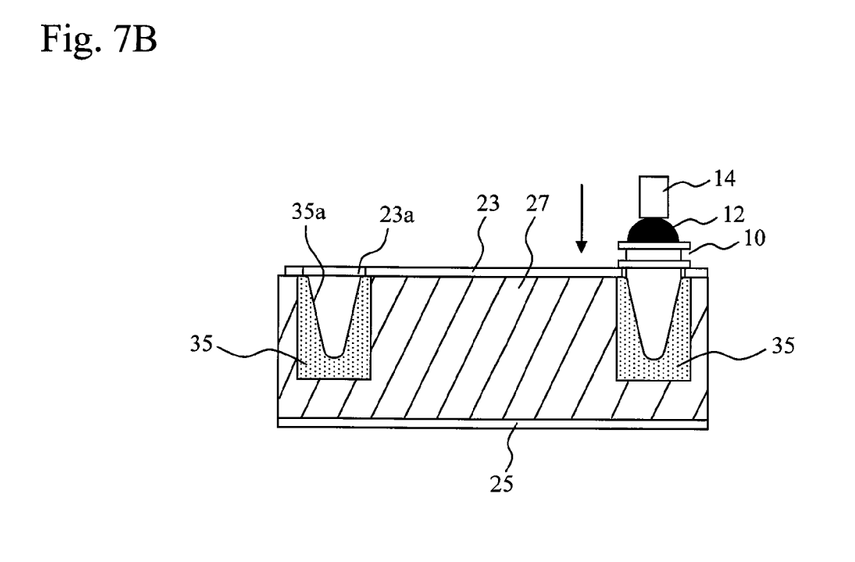
FIG. 7B illustrates a third example of a heat retaining device of an analyzer according to the present invention.

Referring to FIG. 7A and FIG. 7B, the following describes a third example of the heat retaining device of the present invention. The heat retaining device of this example includes a heat retaining body 27, a top plate 23 mounted on the heat retaining body, and a bottom plate 25 mounted under the heat retaining body. The heat retaining body 27 is provided with an elastic body 35. In the heat retaining device of the present example, the heat retaining body 27 is not configured to move vertically. The top plate 23, the bottom plate 25 and the elastic body 35 basically may have the same configuration of the top plate 23, the bottom plate 25 and the elastic body 35 of the third example illustrated in FIG. 7A and FIG. 7B.

FIG. 7A illustrates the state in which the container 10 is disposed in the hole 35a of the elastic body 35. The hole 35a of the elastic body 35 has the inner face of the same shape as the outer face of the conical part 10b of the container 10. Accordingly, in the state in which the container 10 is contained in the hole 35a of the elastic body 35, the conical part 10b of the container 10 is in face-contact with the inner face of the hole 35a of the elastic body. FIG. 7B illustrates the state in which a hermetic-sealing closure fitting device 14 pushes a hermetic-sealing closure 12 into the container 10. The pushing force from the hermetic-sealing closure fitting device 14 to the hermetic-sealing closure 12 acts on the elastic body 35 via the container 10. Since the heat retaining body 27 is fixed, the pushing force from the hermetic-sealing closure fitting device 14 to the hermetic-sealing closure 12 compresses the elastic body 35. When the compressed amount of the elastic body 35 becomes the maximum, the container cannot move further downward. In this way in this example, the elastic force of the elastic body 35 pushes the elastic body 35 against the container 10, so that they come into close contact. When the pushing force from the hermetic-sealing closure fitting device 14 to the hermetic-sealing closure 12 is released, the container 10 is lifted by the elastic force of the elastic body 35 and returns to the original position.

For a better heat-retaining function of a container in a heat retaining device used for an analyzer, contact between the outer face of the conical part 10b of the container and the inner face of the hole 27a has to be made better. To this end, the inner face of the hole 27a of the heat retaining body may have sufficiently small surface roughness. The inner face of the hole 27a of the heat retaining body may be surface treated, for example, may be in a mirror surface form. When the heat retaining body is provided with the elastic body 35, the inner face of the hole 35a of the elastic body 35 may have sufficiently small surface roughness or may be in a mirror surface form.

In the heat retaining device, the outer face of the conical part 10b of the container adheres to the inner face of the hole 35a on the inner face of the hole 27a of the heat retaining body in some cases. Such adhesion of the container makes it difficult to take out the container. To cope with this, the heat retaining device of the present invention is equipped with a function for preventing the conical part 10b of the container from adhering. For instance, the inner face of the hole 27a of the heat retaining body may be formed with a coating for preventing the adhesion of the container, e.g., a coating made of fluorine resin. When the heat retaining body is provided with the elastic body 35, the inner face of the hole 35a of the elastic body 35 may be formed with a coating for preventing the adhesion of the container, e.g., a coating made of fluorine resin in a similar manner. The following describes a release function for facilitating taking-out of the container adherent to the heat retaining device.

Figure 8A:
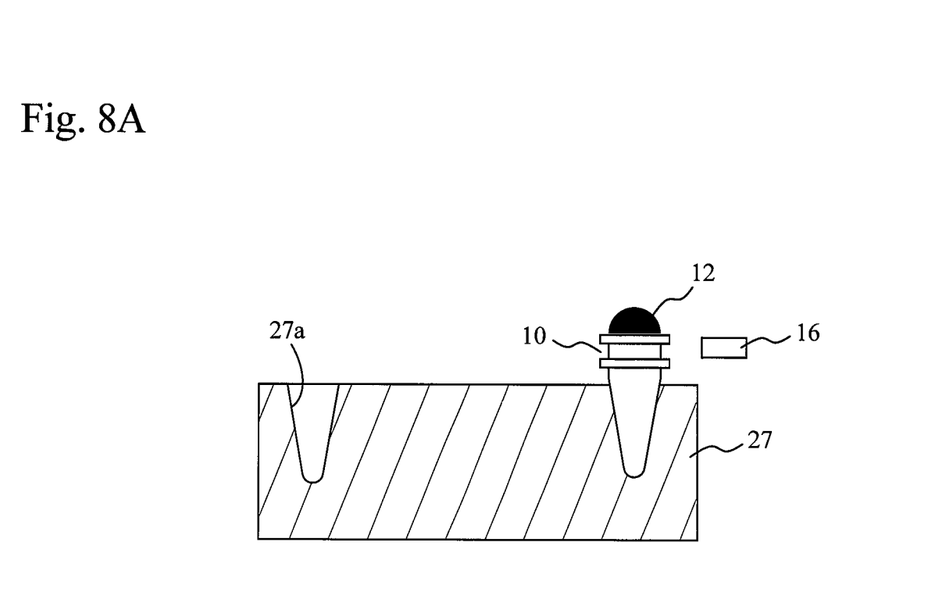
FIG. 8A illustrates a fourth example of a heat retaining device of an analyzer according to the present invention.
Figure 8B:
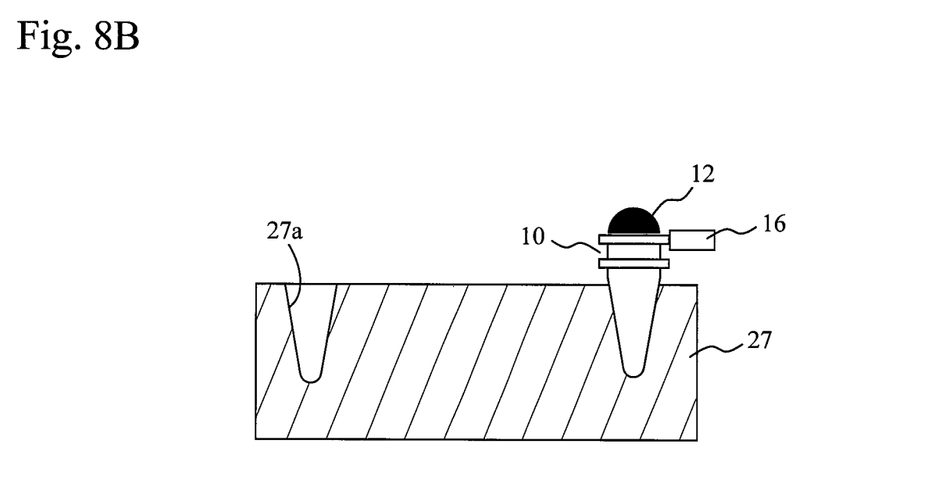
FIG. 8B illustrates a fourth example of a heat retaining device of an analyzer according to the present invention.

Referring to FIG. 8A and FIG. 8B, the following describes a fourth example of the heat retaining device of the present invention. FIG. 8A illustrates the state in which a container 10 is held in a hole 27a of a heat retaining body 27. The container 10 is hermetically sealed by a hermetic-sealing closure 12. The heat retaining device of this example is provided with a vibration/impact device 16 which generates vibration or impact. As illustrated in FIG. 8B, the vibration/impact device 16 is activated to take out the container from the heat retaining body 27 of the heat retaining device. Vibration or impact releases the adhesion between the outer face of the conical part of the container and the inner face of the hole of the heat retaining body. The heat retaining device illustrated in FIG. 8A and FIG. 8B is not provided with a function which moves the heat retaining body 27 vertically. However, this example also may be provided with a supporting spring as in the example illustrated in FIG. 3A and FIG. 3B, for example, to move the heat retaining body 27 vertically. The vibration/impact device 16 may be configured as a part of the robot arm 205 or may be mounted at the robot arm 205.

Figure 9A:
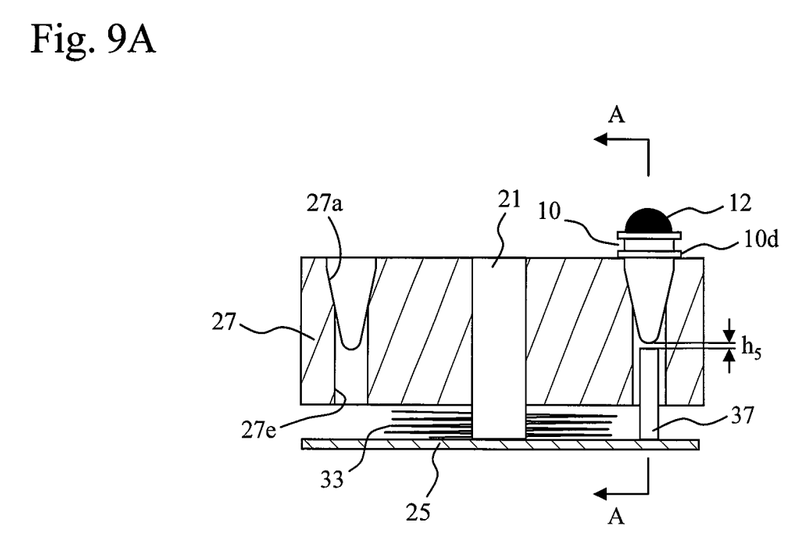
FIG. 9A illustrates a fifth example of a heat retaining device of an analyzer according to the present invention.
Figure 9B:
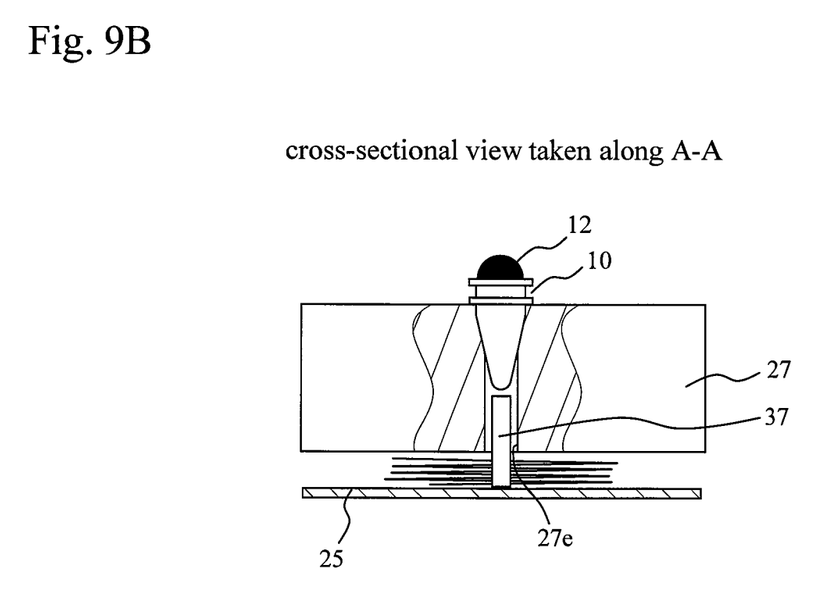
FIG. 9B illustrates a fifth example of a heat retaining device of an analyzer according to the present invention.

Referring to FIG. 9A to FIG. 9D, the following describes a fifth example of the heat retaining device of the present invention. FIG. 9A illustrates a cross-sectional configuration of the heat retaining device of the present example, and FIG. 9B illustrates a cross-sectional configuration of the heat retaining device of the present example viewed from the direction of the arrow A-A of FIG. 9A. The heat retaining device of the present example includes a supporting rod 21, a bottom plate 25 fixed at a lower end of the supporting rod, and a heat retaining body 27 vertically movable along the supporting rod 21. A supporting spring 33 is provided between the heat retaining body 27 and the bottom plate 25.

The heat retaining body 27 is provided with a plurality of holes 27a at an upper face thereof. The heat retaining body 27 is provided with an opening 27e at a bottom face thereof. The holes 27a at the upper face of the heat retaining body 27 are connected to the openings 27e at the bottom face. The openings 27e may be provided at the position of the holes 27a, i.e., an opening may be provided for each hole 27a, or they may be formed as one ring-shaped opening.

To the bottom plate 25 is fixed a rod 37. The rod 37 is disposed in the opening 27e of the heat retaining body 27. The container 10 is held in the hole 27a of the heat retaining body 27. The container 10 is hermetically sealed by the hermetic-sealing closure 12. The flange part 10d of the container 10 comes into contact with the upper face of the heat retaining body 27. The lower end of the container 10 is away from the upper end of the rod 37.

Figure 9C:
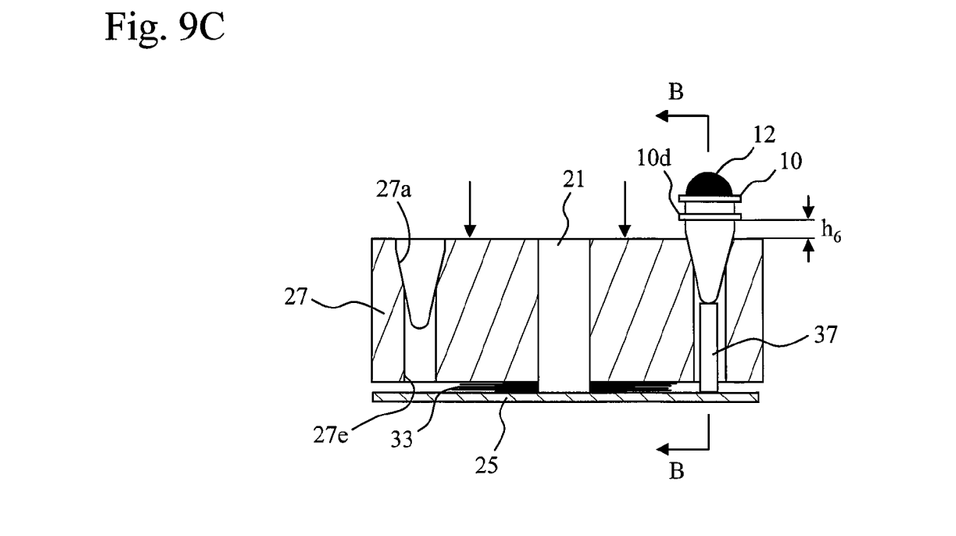
FIG. 9C illustrates a fifth example of a heat retaining device of an analyzer according to the present invention.
Figure 9D:
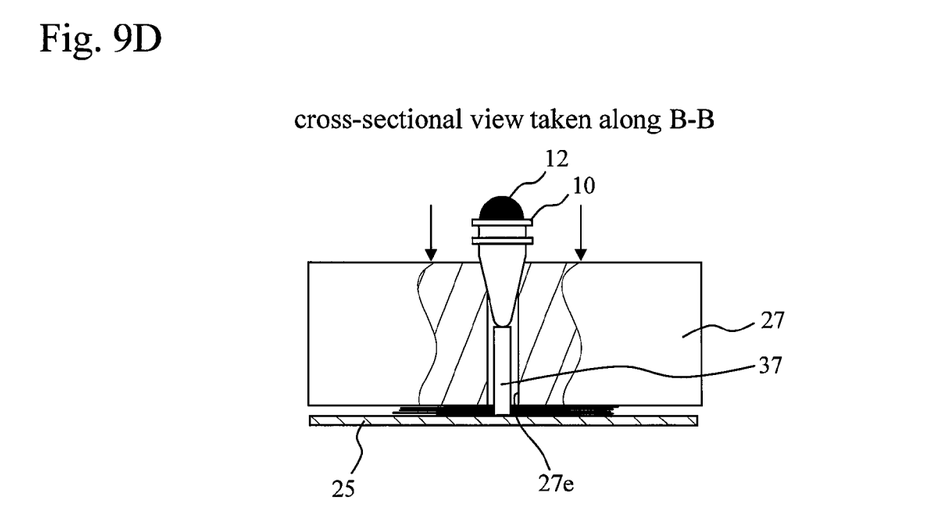
FIG. 9D illustrates a fifth example of a heat retaining device of an analyzer according to the present invention.

FIG. 9C and FIG. 9D illustrate the state of taking out the container 10 from the heat retaining device. In order to take out the container 10, the heat retaining body 27 is moved downward. Means for moving the heat retaining body 27 downward is not described especially. The heat retaining body 27 may be pushed down by a humans' hand or using a tool including a lever.

When the heat retaining body 27 is moved downward, the container 10 contained in the heat retaining body 27 moves downward as well. As a result, the lower end of the container 10 comes into contact with the upper end of the rod 37. When the heat retaining body 27 is further moved downward, the container 10 is lifted relative to the heat retaining body 27. That is, the container 10 is detached from the hole 27a of the heat retaining body 27. In the present example, even when the container 10 adheres to the hole 27a of the heat retaining body 27, the container 10 can be easily detached from the heat retaining body 27.

In the state before the heat retaining body 27 moving downward, let that a gap between the lower end of the container 10 and the upper end of the rod 37 is h5. In the state in which the heat retaining body 27 is moved downward, let that the dimension of the gap between the flange part 10d of the container 10 and the upper face of the heat retaining body 27 is h6. Then, the descent amount of the heat retaining body 27 is h5+h6. In this way, according to the present example, the descent of the heat retaining body 27 makes it easy to detach the container 10 from the heat retaining body 27 even when the container 10 adheres to the heat retaining body 27. When the force moving the heat retaining body 27 downward is released, the heat retaining body 27 returns to the original position by the elastic force of the supporting spring 33.

Figure 10A:
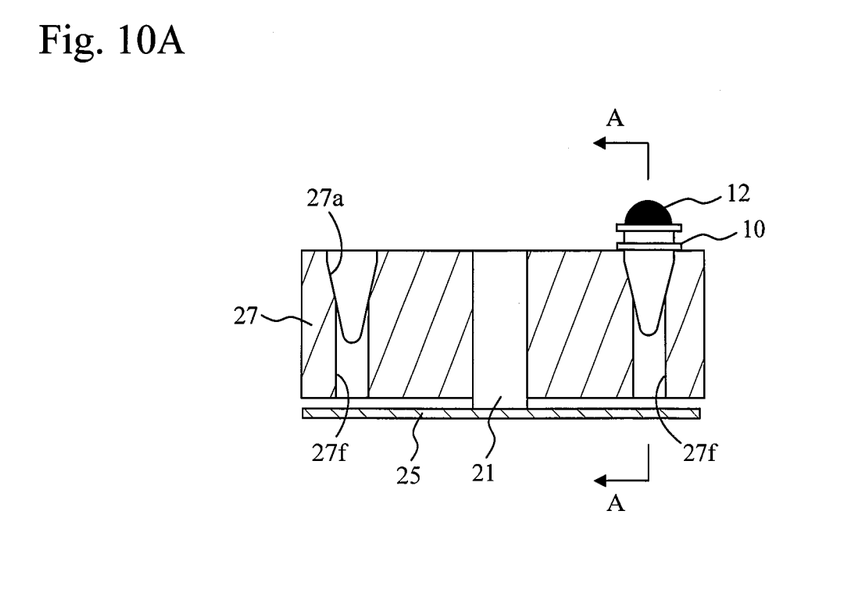
FIG. 10A illustrates a sixth example of a heat retaining device of an analyzer according to the present invention.
Figure 10B:
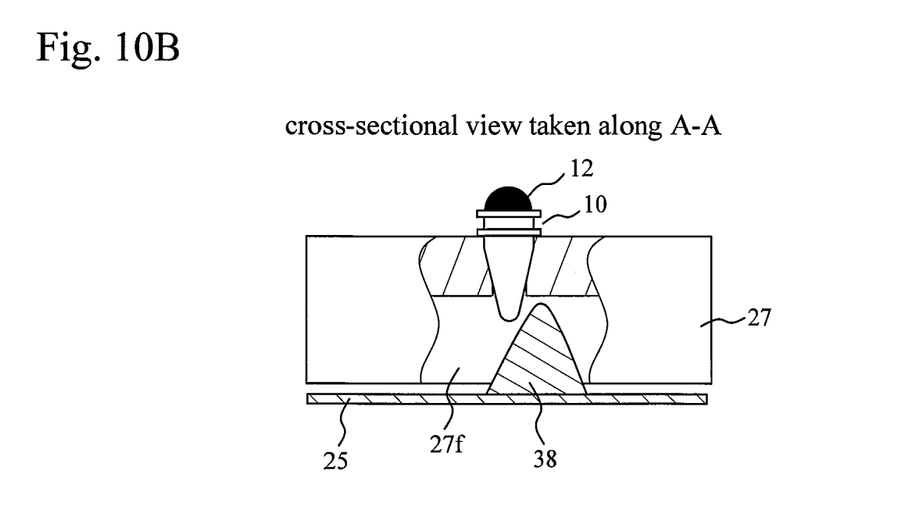
FIG. 10B illustrates a sixth example of a heat retaining device of an analyzer according to the present invention.

Referring to FIG. 10A to FIG. 10D, the following describes a sixth example of the heat retaining device of the present invention. FIG. 10A illustrates a cross-sectional configuration of the heat retaining device of the present example. FIG. 10B is a partially cutaway cross-sectional view of the heat retaining device of the present example taken along a cylindrical face thereof, viewed from the direction of the arrow A-A of FIG. 10A. The heat retaining device of the present example includes a supporting rod 21, a bottom plate 25 fixed at a lower end of the supporting rod, and a heat retaining body 27 rotatable around the supporting rod 21.

The heat retaining body 27 is provided with a plurality of holes 27a at an upper face thereof. The heat retaining body 27 is provided with a ring-shaped opening 27f at a bottom face thereof. The holes 27a at the upper face of the heat retaining body 27 are connected to the opening 27f at the bottom face.

A cam protrusion 38 is fixed at the bottom plate 25. The cam protrusion 38 is disposed in the opening 27f of the heat retaining body 27. The cam protrusion 38 includes a slope-shaped cam face on each side or one of the sides. A container 10 is held in the hole 27a of the heat retaining body 27. The container 10 is hermetically sealed by a hermetic-sealing closure 12. The flange part 10d of the container 10 comes into contact with the upper face of the heat retaining body 27. The position of the container 10 deviates from the position of the cam protrusion 38 in the circumferential direction. The lower end of the container 10 is away from the upper end of the cam protrusion 38.

Figure 10C:
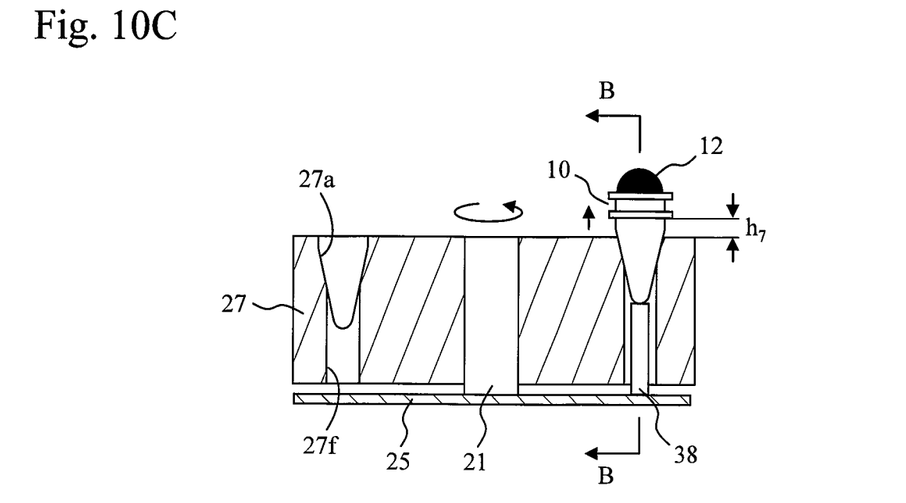
FIG. 10C illustrates a sixth example of a heat retaining device of an analyzer according to the present invention.
Figure 10D:
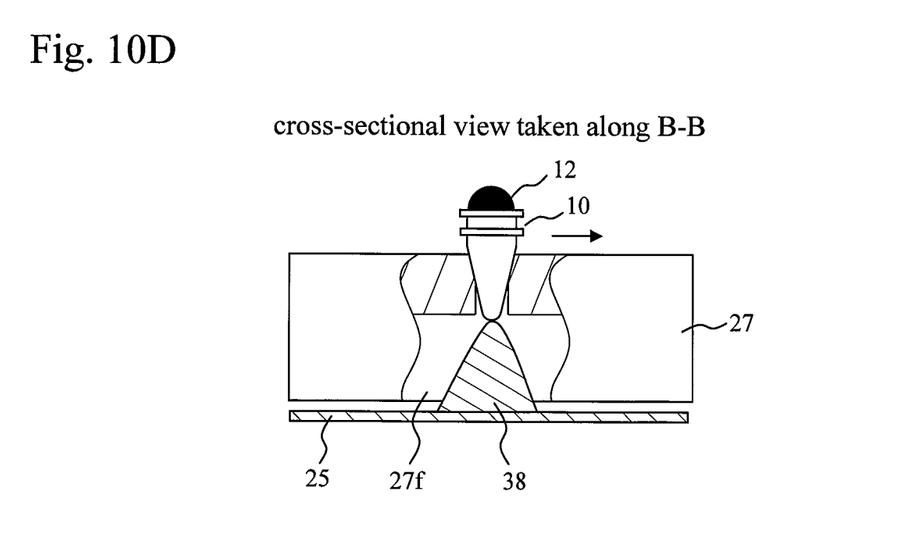
FIG. 10D illustrates a sixth example of a heat retaining device of an analyzer according to the present invention.

FIG. 10C and FIG. 10D illustrate the state of taking out the container 10 from the heat retaining device. In order to take out the container 10, the heat retaining body 27 is rotated. Means for rotating the heat retaining body 27 is not described especially. The heat retaining body 27 may be rotated by a humans' hand. A motor may be used therefor, of course.

The rotation of the heat retaining body 27 brings the lower end of the container 10 into contact with the cam face of the cam protrusion 38. The further rotation of the heat retaining body 27 lifts the container 10 relative to the heat retaining body 27 by a cam function between the lower end of the container 10 and the cam protrusion 38. That is, the container 10 is detached from the hole 27a of the heat retaining body 27. In the present example, the container 10 can be detached from the heat retaining body 27 easily even when the container 10 adheres to the hole 27a of the heat retaining body 27.

In the state in which the container 10 is lifted from the heat retaining body 27, let that the dimension of a gap between the flange part 10d of the container 10 and the upper face of the heat retaining body 27 is h7. The dimension h7 of the gap equals the lifted amount of the container 10 by a cam function between the lower end of the container 10 and the cam protrusion 38. In this way, according to the present example, the rotation of the heat retaining body 27 allows the container 10 to be detached from the heat retaining body 27 easily even when the container 10 adheres to the heat retaining body 27. In this example, the cam protrusion 38 includes a slope-shaped cam face on each side. Therefore, the heat retaining body 27 can be rotated in either directions including right and left. When the slope-shaped cam face is provided on one side of the cam protrusion 38, the rotation direction of the heat retaining body 27 is one direction.

In the sixth example described referring to FIG. 10A to FIG. 10D, a supporting spring is not provided between the heat retaining body 27 and the bottom plate 25. However, in this example also, a supporting spring may be provided between the heat retaining body 27 and the bottom plate 25.

That is the description on examples of the present invention. Those skilled in the art would readily appreciate that the present invention is not limited to the aforementioned examples and may be modified variously within the scope of the invention recited in the appended claims.

DESCRIPTION OF REFERENCE NUMBERS

10 . . . Container, 10a . . . Cylindrical Part, 10b . . . Conical Part, 10c, 10d . . . Flange Part, 12 . . . Hermetic-Sealing Closure, 14 . . . Hermetic-Sealing Closure Fitting Device, 16 . . . Vibration/Impact Device, 20 . . . Heat retaining device, 21 . . . Supporting rod, 23 . . . Top Plate, 23a . . . Opening, 25 . . . Bottom Plate, 27 . . . Heat retaining body, 27a . . . Hole, 27b . . . Opening, 27c . . . Center Opening, 27e, 27f . . . Opening, 31, 33 . . . Supporting Spring, 35 . . . Elastic Body, 35a . . . Hole, 37 . . . Rod, 38 . . . Cam Protrusion, 100 . . . Analyzer, 101 . . . Reaction Container, 102 . . . Reaction Container Storage Unit, 103 . . . Reaction Container Disposal Unit, 105 . . . Chip, 106 . . . Chip Storage Unit, 107 . . . Chip Disposal Unit, 108 . . . Reagent Container, 109 . . . Reagent Container Storage Unit, 110 . . . Specimen Container, 111 . . . Specimen Container Storage Unit, 201 . . . Heat retaining device, 202 . . . Hermetic-Sealing Closure Fitting Device, 203 . . . Agitator, 204 . . . Detector, 205 . . . Robot Arm, 206 . . . Rail, 207 . . . Dispenser, 208 . . . Reaction Container Gripper

The invention claimed is:

1. A heat retaining device configured to retain a container containing a sample therein at a predetermined temperature, comprising:
   a supporting rod;
   a top plate mounted at an upper end of the supporting rod;
   a bottom plate mounted at a lower end of the supporting rod;
   a heat retaining body movable along the supporting rod; and
   a supporting spring provided between the heat retaining body and the bottom plate,
   wherein
   the heat retaining body includes a hole at an upper face thereof, the hole being configured to contain the container therein and having an inner face shaped corresponding to a shape of an outer face of the container, and
   a pressing force applied to the container contained in the hole of the heat retaining body compresses the supporting spring to move the heat retaining body downward along the supporting rod, and release of the pressing force moves the heat retaining body upward by an elastic force of the supporting spring until the heat retaining body comes into contact with the top plate.

2. The heat retaining device according to claim 1, wherein the top plate includes an opening, the opening having an inner diameter larger than an outer diameter of a body part of the container and smaller than an outer diameter of a flange part of the container.

3. The heat retaining device according to claim 2, wherein the container is configured so that, when the container contained in the hole of the heat retaining body is pushed down, the flange part of the container is pushed against the top plate.

4. The heat retaining device according to claim 1, wherein the heat retaining body includes a center opening through which the supporting rod penetrates, the center opening having an inner diameter larger than an outer diameter of the supporting rod so that the heat retaining body tilts when the heat retaining body is moved downward along the supporting rod.

5. The heat retaining device according to claim 1, wherein the heat retaining body includes an elastic body at an upper face thereof, the elastic body including, at an upper face thereof, the hole configured to contain the container therein, the hole having an inner face shaped corresponding to a shape of an outer face of the container.

6. The heat retaining device according to claim 1, wherein the hole of the heat retaining body includes a coating formed on an inner face thereof, the coating being configured to prevent the container from adhering.

7. The heat retaining device according to claim 1, further comprising:
   a vibration/impact device configured to apply vibration or impact to the container contained in the hole of the heat retaining body.

8. The heat retaining device according to claim 1, wherein the bottom plate is provided with a rod, and the heat retaining body includes an opening at a lower face thereof, the opening being connected to the hole at the upper face of the heat retaining body, the rod being disposed in the opening, and
   when the heat retaining body is moved downward along the supporting rod, the container contained in the hole of the heat retaining body comes into contact with the rod, thereby lifting the container from the hole of the heat retaining body.

9. The heat retaining device according to claim 1, wherein the bottom plate is provided with a cam protrusion, and the heat retaining body includes an opening at a lower face thereof, the opening being connected to the hole at the upper face of the heat retaining body, and the cam protrusion being disposed in the opening, and
   when the heat retaining body rotates around the supporting rod, the container contained in the hole of the heat retaining body is lifted from the hole of the heat retaining body by a cam function between the cam protrusion and the container.

10. A heat retaining device configured to retain a container containing a sample therein at a predetermined temperature, comprising:
    a heat retaining body having an upper face;
    an opening part in the upper face of the heat retaining body;
    an elastic body embedded in the opening part and having an upper face, the upper face of the elastic body being positioned at the same level as the upper face of the heat retaining body; and
    a top plate positioned to cover the upper face of the heat retaining body, wherein the elastic body includes a hole at the upper face thereof, the hole being configured to contain the container therein and having an inner face shaped corresponding to a shape of an outer face of the container, wherein a pressing force, which is applied to a hermetic-sealing closure to be fitted to the container fitted in the hole of the elastic body, compresses the elastic body to move the container downward, wherein release of the pressing force returns the elastic body to an original state and returns the container to an original position, and wherein the downward movement of the container brings the container into contact with the top plate.

11. The heat retaining device according to claim 10, wherein the hole of the elastic body includes a coating formed at an inner face thereof, the coating being configured to prevent the container from adhering.

12. A heat retaining device configured to retain a container containing a sample therein at a predetermined temperature, comprising:

a supporting rod;
a top plate mounted at an upper end of the supporting rod;
a bottom plate mounted at a lower end of the supporting rod;
a heat retaining body disposed between the top plate and the bottom plate, the heat retaining body including a hole shaped corresponding to a shape of an outer face of the container; and
a release mechanism which detaches the container contained in the hole of the heat retaining body from the hole of the heat retaining body.

13. The heat retaining device according to claim 12, wherein the release mechanism includes a rod provided at the bottom plate and an opening at a lower face of the heat retaining body, the opening being connected to the hole at the upper face of the heat retaining body, and the rod being disposed in the opening, and when the heat retaining body is moved downward along the supporting rod, the container contained in the hole of the heat retaining body comes into contact with the rod, thereby lifting the container from the hole of the heat retaining body.

14. The heat retaining device according to claim 12, wherein the release mechanism includes a cam protrusion provided at the bottom plate and an opening at a lower face of the heat retaining body, the opening being connected to the hole at the upper face of the heat retaining body, and the cam protrusion being disposed in the opening, and when the heat retaining body rotates around the supporting rod, the container contained in the hole of the heat retaining body is lifted from the hole of the heat retaining body by a cam function between the cam protrusion and the container.

15. An analyzer comprising:

a heat retaining device configured to retain a container containing a sample therein at a predetermined temperature;
a hermetic-sealing closure fitting device to fit a hermetic-sealing closure to the container; and
a detector to detect a reaction product contained in the container, wherein the heat retaining device includes a supporting rod, a top plate mounted at an upper end of the supporting rod, a bottom plate mounted at a lower end of the supporting rod, a heat retaining body movable along the supporting rod, and a supporting spring provided between the heat retaining body and the bottom plate, the heat retaining body includes a hole at an upper face thereof, the hole being configured to contain the container therein and having an inner face shaped corresponding to a shape of an outer face of the container, and when a hermetic-sealing closure is fitted to the container contained in the hole of the heat retaining body by the hermetic-sealing closure fitting device, a pressing force applied from the hermetic-sealing closure fitting device to the hermetic-sealing closure compresses the supporting spring to move the heat retaining body downward along the supporting rod, and release of the pressing force moves the heat retaining body upward by an elastic force of the supporting spring until the heat retaining body comes into contact with the top plate.

16. The analyzer according to claim 15, wherein the top plate includes an opening, the opening having an inner diameter larger than an outer diameter of a body part of the container and smaller than an outer diameter of a flange part of the container.

17. The analyzer according to claim 16, wherein the container is configured so that, when the container contained in the hole of the heat retaining body is pushed down, the flange part of the container is pushed against the top plate.

18. The analyzer according to claim 15, further comprising:

a release mechanism which detaches the container contained in the hole of the heat retaining body from the hole of the heat retaining body.

19. The analyzer according to claim 18, wherein the release mechanism includes a rod provided at the bottom plate and an opening at a lower face of the heat retaining body, the opening being connected to the hole at the upper face of the heat retaining body, and the rod being disposed in the opening, and when the heat retaining body is moved downward along the supporting rod, the container contained in the hole of the heat retaining body comes into contact with the rod, thereby lifting the container from the hole of the heat retaining body.

20. The analyzer according to claim 18, wherein the release mechanism includes a cam protrusion provided at the bottom plate and an opening at a lower face of the heat retaining body, the opening being connected to the hole at the upper face of the heat retaining body, and the cam protrusion being disposed in the opening, and when the heat retaining body rotates around the supporting rod, the container contained in the hole of the heat retaining body is lifted from the hole of the heat retaining body by a cam function between the cam protrusion and the container.

21. A heat retaining device configured to retain a container containing a sample therein at a predetermined temperature, comprising:

a heat retaining body;
an elastic body provided at an upper face of the heat retaining body, the elastic body including a hole at an upper face thereof, the hole being configured to contain the container therein and having an inner face shaped corresponding to a shape of an outer face of the container, wherein a pressing force applied to a hermetic-sealing closure so as to be fitted to the container fitted in the hole of the elastic body compresses the elastic body, and release of the pressing force returns the elastic body to an original state and returns the container to an original position; and a vibration/impact device configured to apply one of vibration and impact to the container held in the hole of the elastic body.

22. A heat retaining device configured to retain a container containing a sample therein at a predetermined temperature, comprising:

a supporting rod;

a top plate mounted at an upper end of the supporting rod;

a bottom plate mounted at a lower end of the supporting rod;

a heat retaining body movable along the supporting rod;

an elastic body provided at an upper face of the heat retaining body, the elastic body including a hole at an upper face thereof, the hole being configured to contain the container therein and having an inner face shaped corresponding to a shape of an outer face of the container, wherein a pressing force applied to a hermetic-sealing closure to be fitted to the container fitted in the hole of the elastic body compresses the elastic body, and release of the pressing force returns the elastic body to an original state and returns the container to an original position, wherein the bottom plate is provided with a cam protrusion, and the heat retaining body includes an opening at a lower face thereof, the opening being connected to the hole at the upper face of the heat retaining body, and the cam protrusion being disposed in the opening, and when the heat retaining body moves downwardly along the supporting rod, the container stored in the hole of the heat retaining body is lifted from the hole of the heat retaining body by a cam function between the cam protrusion and the container.

* * * * *